United States Patent
Mazume et al.

(10) Patent No.: US 8,968,680 B2
(45) Date of Patent: Mar. 3, 2015

(54) CLEANING DEVICE AND AUTOMATIC ANALYZER

(75) Inventors: Kunihiko Mazume, Shizuoka (JP); Masato Kayahara, Shizuoka (JP); Tsutomu Ishikiriyama, Shizuoka (JP)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 12/816,916

(22) Filed: Jun. 16, 2010

(65) Prior Publication Data

US 2010/0254857 A1 Oct. 7, 2010

Related U.S. Application Data

(63) Continuation of application No. PCT/JP2008/072770, filed on Dec. 15, 2008.

(30) Foreign Application Priority Data

Dec. 18, 2007 (JP) ................. 2007-325812

(51) Int. Cl.
*B01L 3/02* (2006.01)
*G01N 35/04* (2006.01)
*G01N 35/02* (2006.01)
*B01L 99/00* (2010.01)

(52) U.S. Cl.
CPC .............. *G01N 35/04* (2013.01); *G01N 35/025* (2013.01); *B01L 99/00* (2013.01); *G01N 2035/0437* (2013.01)
USPC .......................................... 422/510; 422/509

(58) Field of Classification Search
CPC .. B01L 2200/16; G01N 35/1016; G01N 1/14; G01N 1/34
USPC .............................. 422/510, 82.05, 105, 110
See application file for complete search history.

(56) References Cited

U.S. PATENT DOCUMENTS

| 4,785,407 A | 11/1988 | Sakagami | |
|---|---|---|---|
| 6,267,927 B1 * | 7/2001 | Pomar Longedo et al. | 422/65 |
| 2005/0014274 A1 * | 1/2005 | Lee et al. | 436/49 |

FOREIGN PATENT DOCUMENTS

| EP | 0 769 547 A2 | 4/1997 |
|---|---|---|
| EP | 0 825 444 A2 | 2/1998 |
| JP | 62-133356 A | 6/1987 |

(Continued)

OTHER PUBLICATIONS

International Search Report and Written Opinion from PCT/JP2008/072770, dated Feb. 3, 2009 (in Japanese) (10 pages).

(Continued)

*Primary Examiner* — Natalia Levkovich
(74) *Attorney, Agent, or Firm* — Kilpatrick Townsend & Stockton LLP

(57) ABSTRACT

A cleaning device that cleans a liquid storage part of a vessel for storing liquid. The cleaning device includes: a cleaning liquid discharge nozzle that discharges cleaning liquid to the liquid storage part; a first overflow suction nozzle of which tip is positioned above the tip of the cleaning liquid discharge nozzle, that sucks the liquid containing the cleaning liquid from the liquid storage part; a second overflow suction nozzle of which tip is positioned above the tip of the first overflow suction nozzle, that sucks the liquid containing the cleaning liquid from the liquid storage part; and a clog detecting unit that detects clog in one of the first and second overflow suction nozzles.

14 Claims, 10 Drawing Sheets

(56) References Cited

FOREIGN PATENT DOCUMENTS

| | | |
|---|---|---|
| JP | 63-181864 U | 11/1988 |
| JP | 02-042362 A | 2/1990 |
| JP | 06-230014 A | 8/1994 |
| JP | 06-265558 A | 9/1994 |
| JP | 2006-189259 A | 7/2006 |
| JP | 2006-317331 A | 11/2006 |
| JP | 2007-309739 A | 11/2007 |
| WO | WO 2007/132631 A1 | 11/2007 |

OTHER PUBLICATIONS

Supplementary European Search Report for Application No. EP08862895.3, dated Feb. 21, 2011, 7 pages.

* cited by examiner

CLEANING DEVICE AND AUTOMATIC ANALYZER

CROSS-REFERENCE TO RELATED APPLICATIONS

This application is a continuation of PCT international application Ser. No. PCT/JP2008/072770 filed on Dec. 15, 2008 which designates the United States, incorporated herein by reference, and which claims the benefit of priority from Japanese Patent Application No. 2007-325812, filed on Dec. 18, 2007, incorporated herein by reference.

BACKGROUND OF THE INVENTION

1. Field of the Invention

The present invention relates to a cleaning device that cleans a liquid storage part of a vessel for storing liquid and also relates to an automatic analyzer that includes the cleaning device.

2. Description of the Related Art

Regarding automatic analyzers that cause a specimen and a reagent to react with each other and optically measure the result of the reaction, various technologies are known for cleaning a reaction vessel in which a specimen and a reagent are caused to react with each other. For example, as a technology for automatically preventing the liquid in a reaction vessel from overflowing, a technology is disclosed in which a liquid level sensor that detects the liquid level of liquid is provided. The amount of cleaning liquid to be supplied and the amount of liquid to be sucked is controlled on the basis of the output of the liquid level sensor (for example, see Japanese Patent Application Laid-open No. H6-230014).

SUMMARY OF THE INVENTION

A cleaning device according to an aspect of the present invention that cleans a liquid storage part of a vessel for storing liquid includes: a cleaning liquid discharge nozzle that discharges cleaning liquid to the liquid storage part; a first overflow suction nozzle of which tip is positioned above the tip of the cleaning liquid discharge nozzle, that sucks the liquid containing the cleaning liquid from the liquid storage part; a second overflow suction nozzle of which tip is positioned above the tip of the first overflow suction nozzle, that sucks the liquid containing the cleaning liquid from the liquid storage part; and a clog detecting unit that detects clog in one of the first and second overflow suction nozzles.

An automatic analyzer according to another aspect of the present invention that causes a specimen and a reagent to react with each other and optically measures the result of the reaction to analyze components of the specimen includes the cleaning device according to the above invention as a unit for cleaning a liquid storage part of a reaction vessel in which the specimen and the reagent are caused to react with each other.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Best modes for carrying out the present invention (hereinafter, "EMBODIMENT") are explained below with reference to the accompanying drawings. The drawings referred to in the following explanation are schematic, and thus, in the case where the same object is represented in different drawings, the size or scale may be different.

First Embodiment

Figure 1:
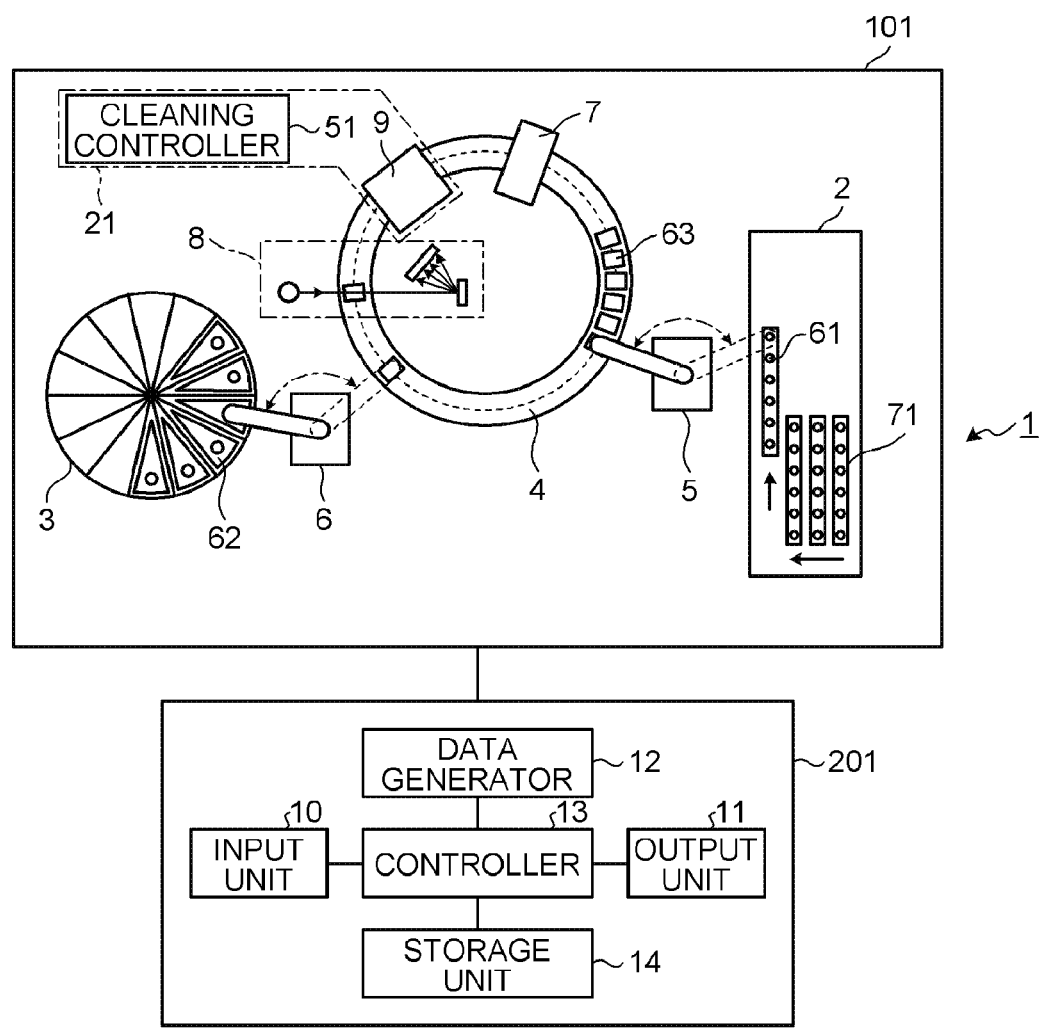
FIG. 1 is a diagram illustrating a configuration of a main part of an automatic analyzer according to a first embodiment of the present invention.

FIG. 1 is a diagram illustrating a configuration of an automatic analyzer according to the first embodiment of the present invention. An automatic analyzer 1 according to the first embodiment of the present invention includes a measuring unit 101 that dispenses a specimen (sample) and a reagent to a reaction vessel and optically measures the reaction caused in the reaction vessel; and a data processing unit 201 that controls the automatic analyzer 1 including the measuring unit 101 and analyzes the result of the measurement performed by the measuring unit 101. The cooperation of these two units allows automatic and successive biological analysis on the components of a plurality of specimens.

The measuring unit 101 includes a specimen vessel holder 2 that stores a plurality of racks 71 on which specimen vessels 61 for storing specimens are set; a reagent vessel holder 3 that holds reagent vessels 62; a reaction vessel holder 4 that holds reaction vessels 63 in which a specimen and a reagent are caused to react with each other; a specimen dispenser 5 that dispenses to the reaction vessel 63 the specimen stored in a specimen vessel 61 held by the specimen vessel holder 2; a reagent dispenser 6 that dispenses to the reaction vessel 63 the reagent stored in the reagent vessel 62 held by the reagent vessel holder 3; a stirring unit 7 that stirs the liquid in the reaction vessel 63; an optical measuring unit 8 that receives a light having been applied from a light source and passed through the reaction vessel 63 and measures the intensity of a predetermined wavelength component; and a reaction vessel cleaner 9 that cleans the reaction vessels 63.

The data processing unit 201 includes an input unit 10 having a keyboard and a mouse and the like to which information necessary for analyzing a specimen and information for operating the automatic analyzer 1 are input; an output unit 11 that includes a display and a printer and outputs information on analysis on a specimen; a data generator 12 that calculates an absorbance of the liquid in the reaction vessel 63 based on the result of measurement by the measuring unit 101 and calculates components of the liquid in the reaction vessel 63 using the result of calculation of the absorbance and various types of information, such as a standard curve and analysis parameters; a controller 13 that controls the automatic analyzer 1; and a storage unit 14 that stores various types of information including information on analysis of the specimen. The data processing unit 201 is implemented by a computer including a CPU, a ROM, and a RAM.

Figure 2:
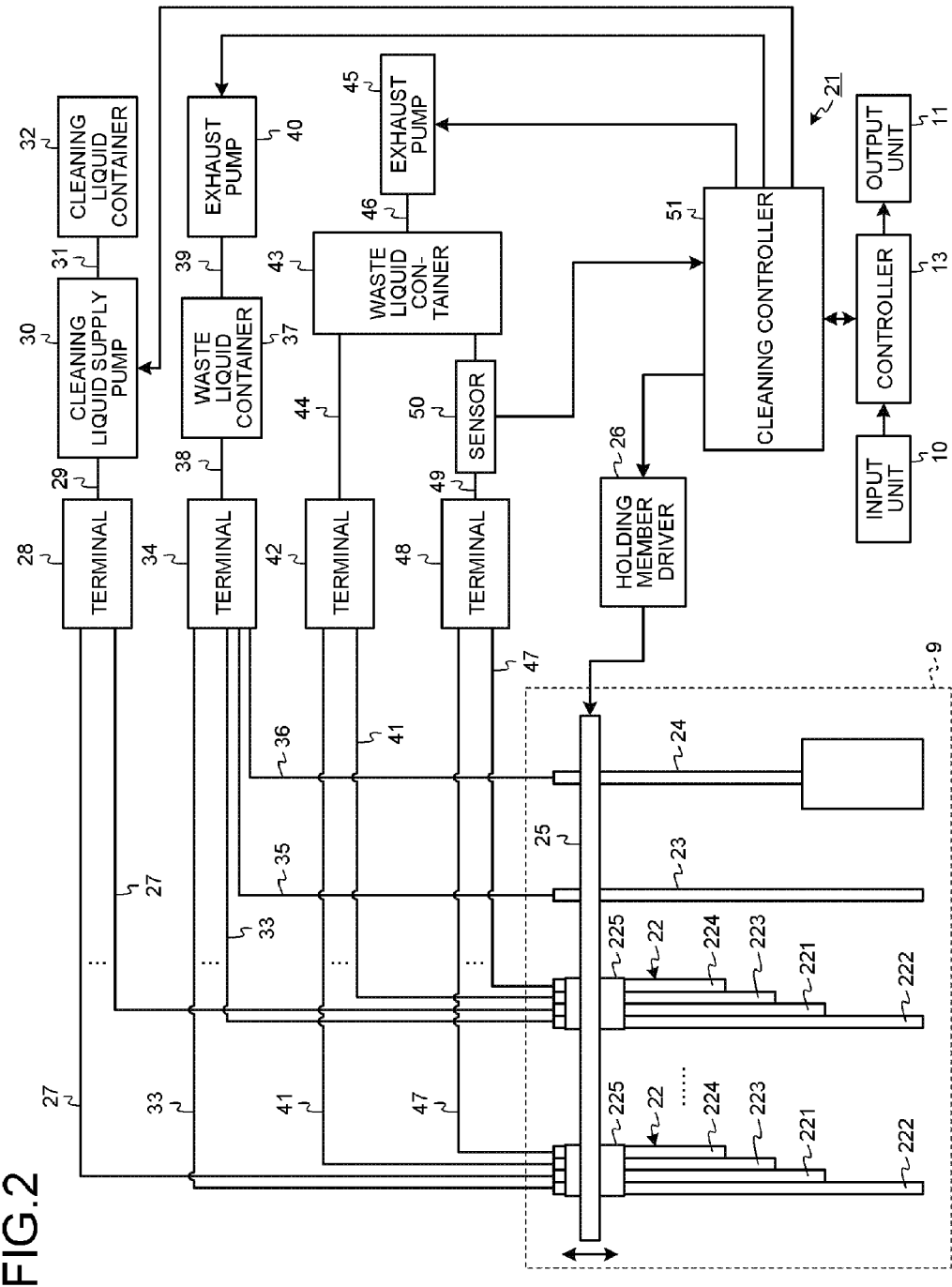
FIG. 2 is a diagram illustrating a main part of a cleaning device according to the first embodiment of the present invention.

FIG. 2 is a diagram illustrating a configuration of a cleaning device according to the first embodiment. A cleaning device 21 is set in the measuring unit 101 of the automatic analyzer 1 and has a function as a cleaner for cleaning the reaction vessel 63. The cleaning device 21 includes a plurality of nozzle groups 22 that discharge the cleaning liquid to the reaction vessel 63 to be cleaned and suck the liquid stored in the reaction vessel 63. Further, the cleaning device 21 includes a cleaning liquid suction nozzle 23 that sucks the cleaning liquid remaining in the reaction vessel 63 having been cleaned repeatedly by the nozzle groups 22; a drying nozzle 24 that dries the reaction vessel 63 from which the cleaning liquid suction nozzle 23 have sucked the cleaning liquid. Furthermore, the cleaning device 21 includes a platy holding member 25, which holds the nozzle groups 22, the cleaning liquid suction nozzle 23, and the drying nozzle 24, and a holding member driver 26 that drives the holding member 25 vertically.

The nozzle groups 22, the cleaning liquid suction nozzle 23, the drying nozzle 24, and the holding member 25 form the reaction vessel cleaner 9 of the automatic analyzer 1. These nozzles are arranged above the reaction vessels 63 along the circumference of the circular reaction vessel holder 4.

The nozzle group 22 consists of a set of four metal nozzles having different functions, respectively. Specifically, the nozzle group 22 includes a cleaning liquid discharge nozzle 221 that discharges the cleaning liquid to the reaction vessel 63; a liquid suction nozzle 222 of which tip is positioned below the tip of the cleaning liquid discharge nozzle 221 and sucks the liquid stored in the reaction vessel 63; a first overflow suction nozzle 223 of which tip is positioned above the tip of the cleaning liquid discharge nozzle 221 and can suck the liquid stored in the reaction vessel 63; and a second overflow suction nozzle 224 of which tip is positioned above the tip of the first overflow suction nozzle 223 and can suck the liquid stored in the reaction vessel 63. The four nozzles are collectively held by a cover 225 near the base and are provided in parallel from at least the portion held by the cover 225 to their tips. The diameters of the four nozzles are approximately equal. The tip of the liquid suction nozzle 222 is positioned at the same level as those of the tips of the cleaning liquid suction nozzle 23 and the drying nozzle 24.

The cleaning liquid discharge nozzle 221 is connected to a terminal 28 via a tube 27 that forms a flow path of the cleaning liquid. The terminal 28 is connected to a cleaning liquid supply pump 30 that supplies the cleaning liquid via a tube 29. The cleaning liquid supply pump 30 is connected to a cleaning liquid container 32 that reserves the cleaning liquid via a tube 31. The cleaning liquid is sucked by the cleaning liquid supply pump 30 from the cleaning liquid container 32 and transferred to the terminal 28. The terminal 28 has a function of divergently supplying the cleaning liquid transferred from the cleaning liquid supply pump 30 to each of the cleaning liquid discharge nozzles 221.

The liquid suction nozzle 222 is connected to a terminal 34 via a tube 33. The terminal 34 is connected to the cleaning liquid suction nozzle 23 and the drying nozzle 24 respectively via tubes 35 and 36. The terminal 34 is connected via a tube 38 to a waste liquid container 37 for reserving the liquid sucked from the reaction vessel 63. The waste liquid container 37 is connected to an exhaust pump 40 via a tube 39. The exhaust pump 40 generates suction pressures (negative pressure) by which the liquid suction nozzle 222, the cleaning liquid suction nozzle 23, and the drying nozzle 24 suck the liquid. Thus, the liquids sucked respectively by the liquid suction nozzle 222, the cleaning liquid suction nozzle 223, and the drying nozzle 24 are collected in the terminal 34 and transferred to the waste liquid container 37.

The first overflow suction nozzle 223 is connected to a terminal 42 via a tube 41. The terminal 42 is connected to a waste liquid container 43 for reserving the liquid sucked from the reaction vessel 63 via a tube 44. The waste liquid container 43 is connected via a tube 46 to the exhaust pump 45, which generates a suction pressure for the first overflow suction nozzle 223 to suck the liquid. The liquid sucked by the first overflow suction nozzles 223 is collected in the terminal 42 and transferred to the waste liquid container 43.

The second overflow suction nozzle 224 is connected to a terminal 48 via a tube 47. Provided that a side connected to the second overflow suction nozzle 224 is the foreside of the terminal 48, a sensor 50 (clog detecting unit) that detects the flow of liquid in a tube 49 is provided in the middle of the tube 49 of which one end is connected to the rear side of the terminal 48. The sensor 50 is implemented with a photoelectric sensor, such as a photo interrupter. The other end of the tube 49 is connected to the waste liquid container 43. Thus, a suction operation of the second overflow suction nozzle 224 synchronizes with a suction operation of the first overflow suction nozzle 223. The position where the sensor 50 is set may be in the terminal 48 or the foreside of the terminal 48.

The cleaning liquid supply pump 30 and the exhaust pumps 40 and 45 are driven under the control of a cleaning controller 51 that performs driving control of the cleaning device 21. The cleaning controller 51 controls operations of the cleaning device 21 in cooperation with the controller 13 of the data processing unit 201. In this sense, the controller 13 and the cleaning controller 51 form at least a part of an operation control unit that controls operations of the automatic analyzer 1.

Figure 3:
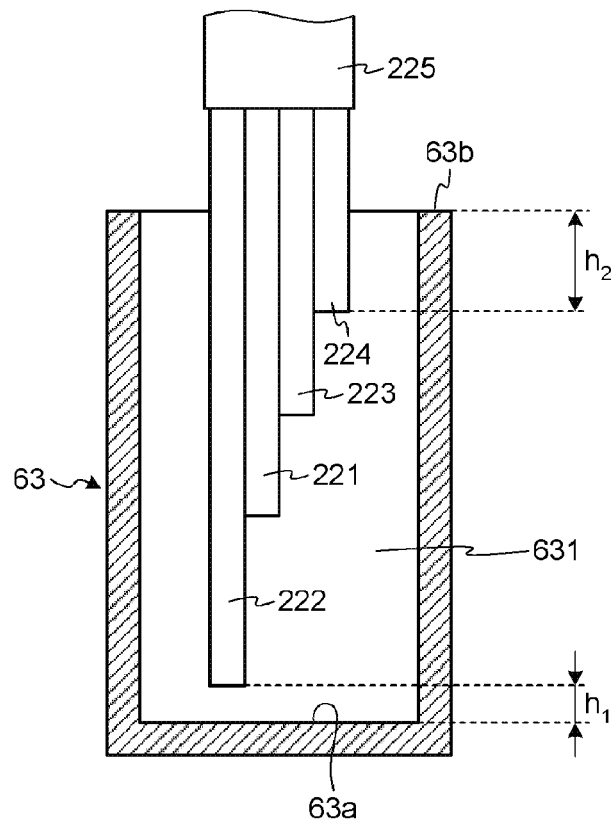
FIG. 3 is a diagram illustrating a state where a group of nozzles enters a liquid storage part of a reaction vessel and stops.

FIG. 3 is a diagram illustrating a state where, when the cleaning device 21 cleans the reaction vessel 63, the holding member 25 lowers, so that the tips of the four nozzles forming the nozzle group 22 enter a liquid storage part 631 of the reaction vessel 63 and stop. As shown in FIG. 3, the tip (lower end) of the liquid suction nozzle 222 is positioned higher than a bottom surface 63a of the reaction vessel 63 by $h_1$. The tip of the second overflow suction nozzle 224 is positioned lower than the upper end surface 63b of the reaction vessel 63 by $h_2$. It suffices that the tip of the second overflow suction nozzle 224 is positioned lower than an upper end surface 63b of the reaction vessel 63 when the reaction vessel 63 is cleaned. In consideration for the surface tension of the liquid, the tip of the second overflow suction nozzle 224 may be positioned slightly higher than the upper end surface 63b of the reaction vessel 63 when the reaction vessel 63 is cleansed.

To improve the efficiency in cleaning the reaction vessel 63 by the nozzle group 22, it is desirable that the cleaning liquid reach an upper portion of the reaction vessel 63. In this sense, it is preferable that the position of the tip of the first overflow suction nozzle 223 in the state illustrated in FIG. 3 be close to the upper end surface 63b of the reaction vessel 63.

Figure 4:
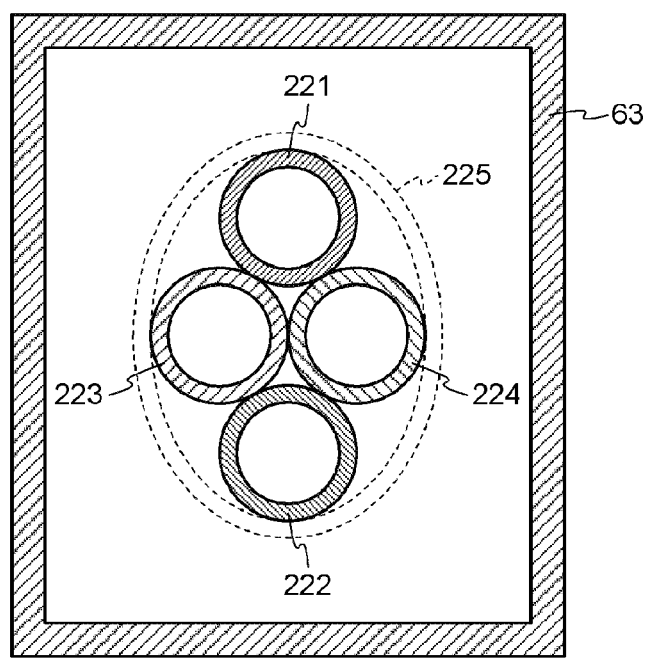
FIG. 4 is a diagram illustrating an accurate positional relationship of four nozzles, which form the nozzle group, in the diametrical direction.

FIG. 4 is a cross-sectional view illustrating an accurate positional relationship of the four nozzles, which form the nozzle group 22, in the diametrical direction. FIG. 4 also illustrates the positional relationship between the four nozzles and the reaction vessel 63 at the time when the reaction vessel 63 is cleaned. Each of the four nozzles makes contact with two other nozzles along the longitudinal direction. The positional relationship between the four nozzles in the diametrical direction is arbitrary. As illustrated in FIG. 4, it is more preferable that the first overflow suction nozzle 223 make contact with the second overflow suction nozzle 224.

Figure 5:
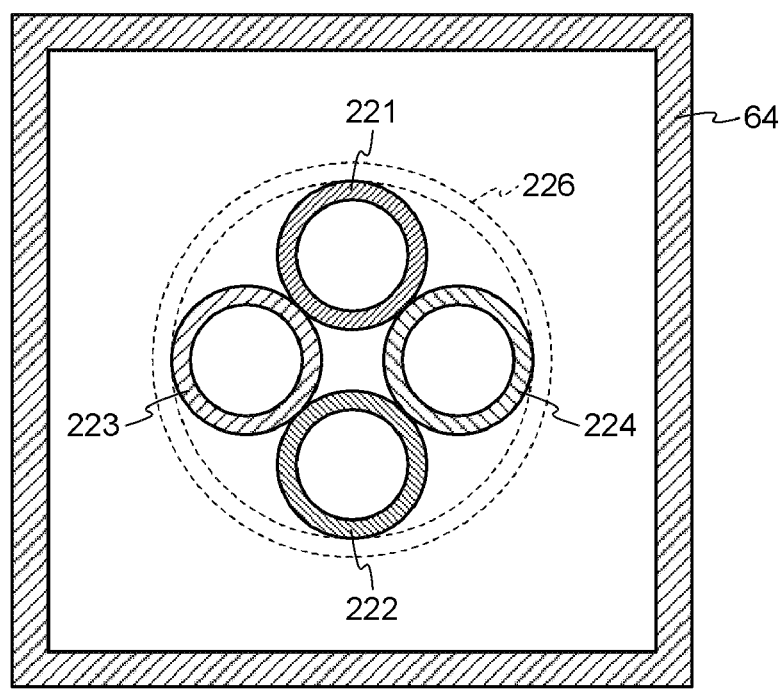
FIG. 5 is a diagram illustrating another example of an accurate positional relationship of four nozzles, which form a nozzle group, in the diametrical direction.

As illustrated in FIG. 4, the cross section of the cover 225 is approximately oval. This is because it is necessary to provide an appropriate clearance between the side surface of the reaction vessel 63 and each nozzle in consideration for an oblong cross section of the reaction vessel 63. The arrangement of the four nozzles and the cross-sectional shape of the cover thus can be changed depending on the cross sectional shape of the reaction vessel to be cleaned. For example, in the case where a reaction vessel 64 of which cross section is square is used, as illustrated in FIG. 5, it suffices that a cover 226 with an approximately circular cross sectional shape holds the four nozzles.

The reaction vessel 63, which is to be cleaned by the cleaning device 21, having the above configuration moves along with the intermittent rotation of the reaction vessel holder 4. In the state where the reaction vessel holder 4 is still, the nozzle group 22 enters the reaction vessel 63 positioned just below the holding member 25 because the holding member 25 lowers (see FIG. 3). Then, the reaction vessel holder 4 discharges the cleaning liquid, and sucks the liquid containing the cleaning liquid. Incidentally, the cleaning device 21 includes the plural nozzle group 22. Thus, discharging of the cleaning liquid and suction of the liquid are repeatedly carried out by the nozzle groups 22 to each reaction vessel 63 with the positional change of the reaction vessel 63 along with rotation of the reaction vessel holder 4 and with the vertical movement of the holding member 25. As a result of the repetition, the reacted liquid of the specimen and the reagent, which is measured by the optical measuring unit 8, is gradually sucked and removed from the liquid storage part 631 of the reaction vessel 63 and accordingly almost only the cleaning liquid remains.

The reaction vessel 63, to and from which discharging of the cleaning liquid and suction of the liquid by the nozzle groups 22 have been completed, moves to a position just below the cleaning liquid suction nozzle 23. Then, the cleaning liquid suction nozzle 23 sucks the remaining cleaning liquid. Thereafter, the reaction vessel 63 moves to a position just below the drying nozzle 24. The drying nozzle 24 absorbs the cleaning liquid attached to the inner wall of the reaction vessel 63, using a prism tip made of resin, in order to dry the reaction vessel 63.

Figure 6:
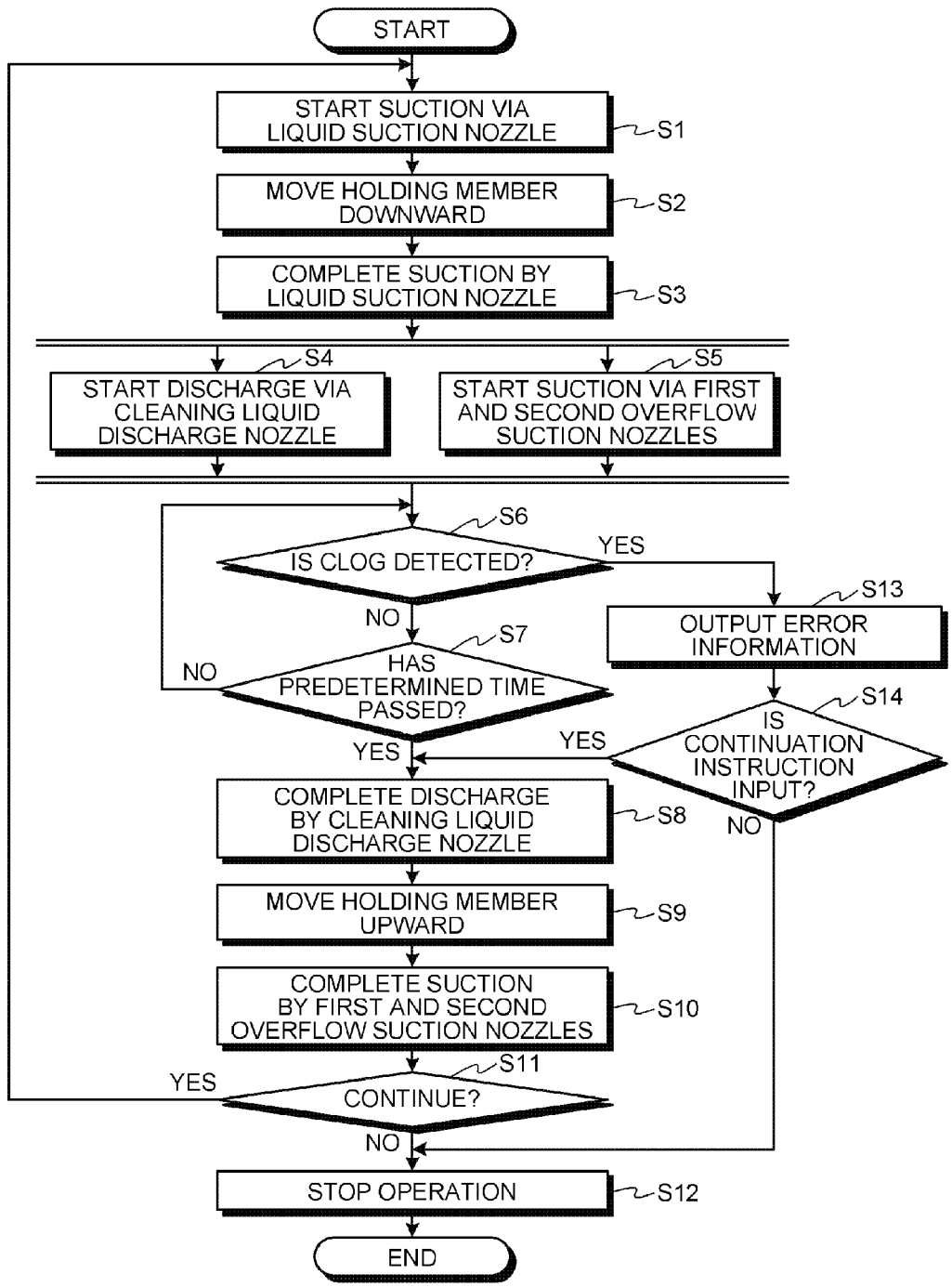
FIG. 6 is a flowchart of an overview of a controlling method of a cleaning operation performed by the automatic analyzer according to the first embodiment of the present invention.

FIG. 6 is a flowchart of an overview of a process performed when the automatic analyzer 1 controls the cleaning operation. The exhaust pump 40 drives to start a suction operation via the liquid suction nozzle 222 (step S1). At this stage, because the exhaust pump 40 is connected to the cleaning liquid suction nozzle 23 and the drying nozzle 24, suction operations via the cleaning liquid suction nozzle 23 and the drying nozzle 24 are started at the same time.

Subsequently, the holding member driver 26 lowers the holding member 25 (step S2). The nozzle groups 22, the cleaning liquid suction nozzle 23, and the drying nozzle 24 enter the reaction vessels 63 each still in a corresponding position. The liquid suction nozzle 222 reaches the liquid level of the liquid in the reaction vessel 63 in the middle of the lowering, and starts actually sucking the liquid.

The exhaust pump 40 stops driving at the time when a predetermined time has elapsed from the start of the operation. This completes the liquid-suction operation of the liquid suction nozzle 222 (step S3). The stop time at step S3 is determined as a time in which at least the liquid in the volume of the liquid storage part 631 can be sucked in consideration for the volume of the reaction vessel 63 and the amount of suction by the exhaust pump 40.

Subsequently, the cleaning liquid supply pump 30 drives to start the operation for discharging the cleaning liquid via the cleaning liquid discharge nozzle 221 (step S4). Also, the exhaust pump 45 drives to start the operation for sucking the liquid via the first overflow suction nozzle 223 and the second overflow suction nozzle 224 (step S5).

Figure 7:
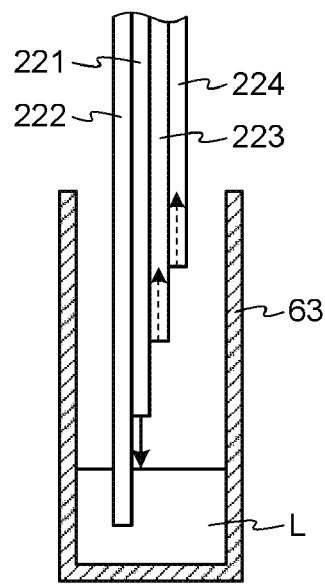
FIG. 7 is a diagram illustrating a state where a cleaning liquid discharge nozzle discharges cleaning liquid to the reaction vessel.

At step S4, once the cleaning liquid discharge nozzle 221 starts discharging the cleaning liquid, the level of a liquid L stored in the reaction vessel 63 rises as illustrated in FIG. 7. In this case, the liquid L, which contains the cleaning liquid discharged by the cleaning liquid discharge nozzle 221, is stirred in the reaction vessel 63 by the discharge pressure of the cleaning liquid discharge nozzle 221. Thus, the attachment on the inner surface of the liquid storage part 631 is cleaned off. In FIG. 7, the level of the liquid L has not risen to the tips of the nozzles. In this situation, the first and the second overflow suction nozzles 223 and 224 do not actually suck the liquid L, although they perform the suction operation depending on the exhaust pump 45.

Figure 8:
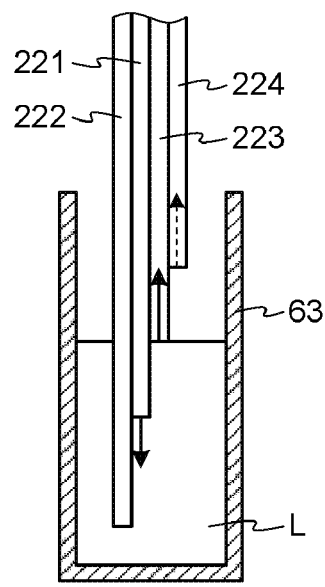
FIG. 8 is a diagram illustrating a state in the cleaning device according to the first embodiment of the present invention where, while the cleaning liquid discharge nozzle discharges the cleaning liquid to the reaction vessel, a first overflow suction nozzle sucks the liquid.
Figure 9:
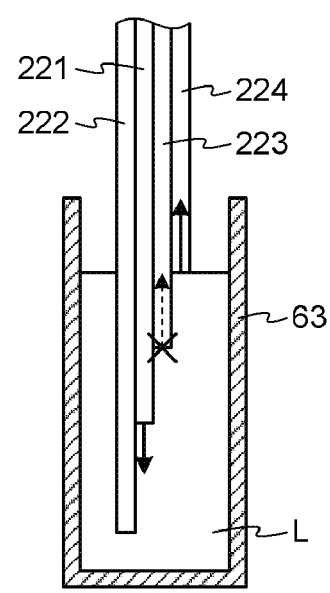
FIG. 9 is a diagram illustrating a state in the cleaning device according to the first embodiment of the present invention where, while the cleaning liquid discharge nozzle discharges the cleaning liquid to the reaction vessel, clog is caused in the first overflow suction nozzle and a second overflow suction nozzle sucks the liquid.

Thereafter, once the level of the liquid L rises to the tip of the first overflow suction nozzle 223, the first overflow suction nozzle 223 starts sucking the liquid L as illustrated in FIG. 8. While the first overflow suction nozzle 223 functions normally and sucks the liquid L, the level of the liquid L does not rise more. In this case, because the second overflow suction nozzle 224 does not suck the liquid L, the sensor 50 does not detect the flow of the liquid L. Thus, clog in the first overflow suction nozzle 223 is not detected (NO at step S6).

When clog in the first overflow suction nozzle 223 is not detected and the predetermined time has passed (YES at step S7), the cleaning liquid supply pump 30 stops its operation to complete discharging of the liquid L by the cleaning liquid discharge nozzle 221 (step S8). On the contrary, when clog in the first overflow suction nozzle 223 is not detected and the predetermined time has not passed (NO at step S7), the operation goes back to step S6.

After the operation of the cleaning liquid discharge nozzle 221 for discharging the liquid L ends, the holding member driver 26 elevates the holding member 25 (step S9). Subsequently, the exhaust pump 45 stops driving, and this completes the suction operation by the first overflow suction nozzle 223 and the second overflow suction nozzle 224 (step S10).

In this manner, a series of cleaning process by the nozzle group 22 with respect to one reaction vessel 63 completes. When the cleaning device 21 continues the cleaning process, i.e., the cleaning device 21 continues performing the cleaning process on another reaction vessel 63 (YES at step S11), the operation goes back to step S1. On the contrary, when the cleaning device 21 does not continue performing the cleaning process (NO at step S11), the operations of the automatic analyzer 1 that includes the cleaning device 21 stop (step S12) and a series of processes completes.

Subsequently, the case where clog in the first overflow suction nozzle 223 is detected at step S6 (YES at step S6) is explained. In the reaction vessel 63 where clog is caused in the first overflow suction nozzle 223, the level of the liquid L rises higher than the tip of the first overflow suction nozzle 223. Once the level of the liquid L reaches the tip of the second overflow suction nozzle 224, the second overflow suction nozzle 224 starts sucking the liquid L, and thus the level of the liquid L stops rising. Once the second overflow suction nozzle 224 starts sucking the liquid L, the sensor 50 detects the flow of the liquid L and sends a sensor signal to the cleaning controller 51.

The cleaning controller 51 that has received the sensor signal sends a signal notifying the reception of the sensor signal to the controller 13. Upon receipt of the sensor signal, the controller 13 causes the output unit 11 to output error information representing that clog in the first overflow suction nozzle 223 is detected (step S13).

It is preferable that, when outputting the error information, the output unit 11 output information requesting an input of an instruction signal for an instruction on whether to continue the cleaning operation. The second overflow suction nozzle 224 can perform the function instead of the first overflow suction nozzle 223. Thus, it is less possible that the liquid immediately overflow from the reaction vessel 63 even if the first overflow suction nozzle 223 gets clogged. Thus, the process for inquiring whether the cleaning operation is to be continued can be performed.

Figure 10:
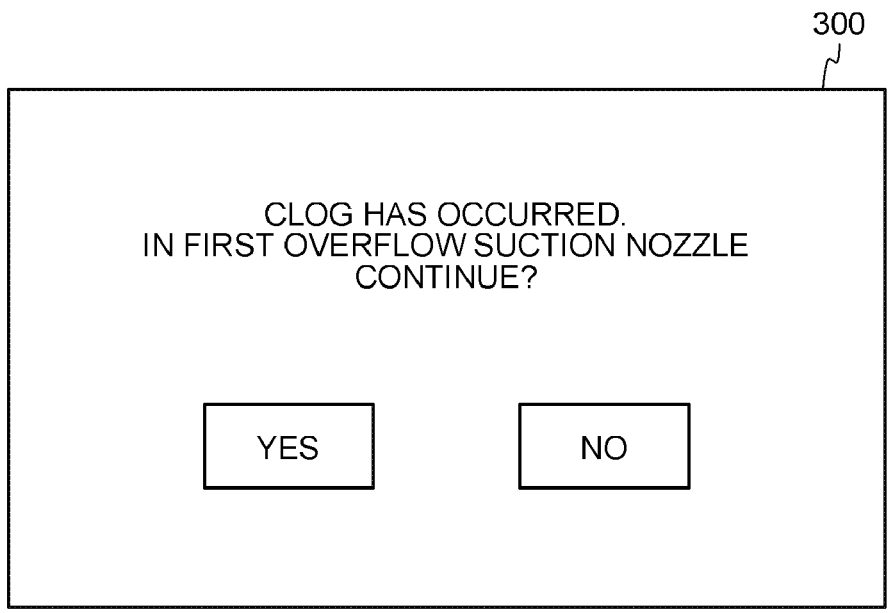
FIG. 10 is a diagram illustrating an example of display output on an error information display screen.

FIG. 10 is a diagram illustrating an example of display output of error information on the display of the output unit 11. A user who watches an error information display screen 300 selects and inputs whether to continue the operation, using the input unit 10.

When an instruction signal for continuing the process is input via the input unit 10 (YES at step S14), the processes of and after the above-described step S8 are sequentially performed in the automatic analyzer 1. On the other hand, when an instruction signal for stopping the process is input via the input unit 10 (NO at step S14), the operation of the automatic analyzer 1 that includes the cleaning device 21 stops (step S12) and a series of processes completes.

Figure 11:
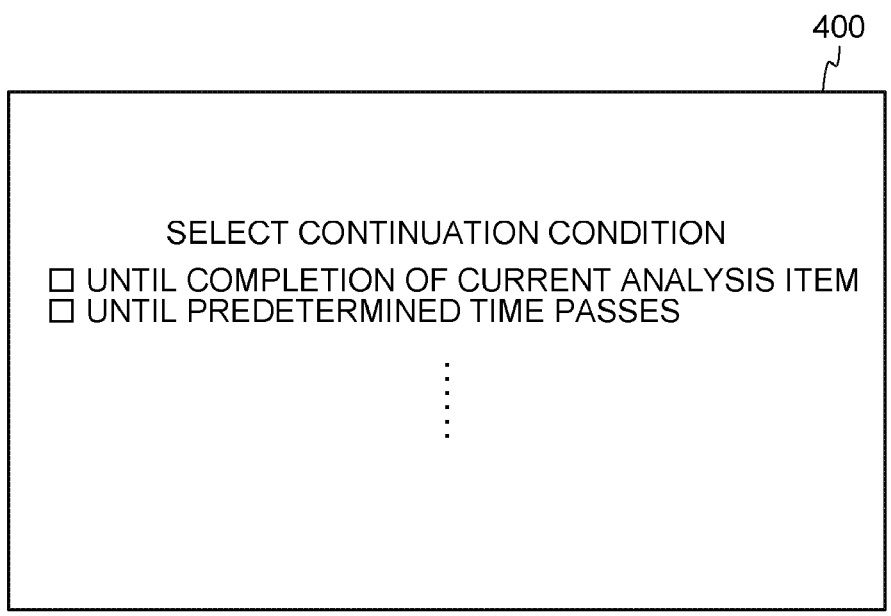
FIG. 11 is a diagram illustrating an example of display output on a continuation condition input screen.

The process performed by the automatic analyzer 1 when the instruction signal of an instruction for continuing the process is input at step S14 is merely provisional. Therefore, it is desirable that a limit is previously imposed on the process to be continued by the automatic analyzer 1 when the clog occurs in the first overflow suction nozzle 223. For example, after the instruction signal for continuing the process is input from the input unit 10, the output unit 11 may output and display a continuation condition input screen 400 illustrated in FIG. 11, as a request for a user to select and input a continuation condition. The continuation condition, which is input in response to the request, is a reference for determining whether the cleaning device 21 continues the cleaning operation at step S11.

After the cleaning device 21 stops its operation, the user performs maintenance of the automatic analyzer 1 that includes the cleaning device 21. Specifically, the user detaches the reaction vessel cleaner 9 from the measuring unit 101 and cleans the various nozzles including the first overflow suction nozzle 223 to remove the clog therefrom.

When the user performs maintenance of the cleaning device 21, the reaction vessel cleaner 9 is detached from the body of the measuring unit 101. Therefore, all of the first overflow suction nozzles 223 are collectively cleaned. Thus, the sensor 50 is not required to identify which first overflow suction nozzle 223 out of the first overflow suction nozzles 223 gets clogged. In other words, in the first embodiment, it suffices that only one sensor 50 be provided.

According to the first embodiment of the present invention explained above, the two overflow suction nozzles are provided that can suck the liquid containing the cleaning liquid discharged to the liquid storage part of the vessel for storing the liquid. Therefore, even if one of the overflow suction nozzles gets clogged, suction of the liquid can be continued with the other overflow suction nozzle. This definitely prevents the liquid, such as the cleaning liquid, from overflowing from the reaction vessel, which extends the life of the overflow suction nozzles.

According to the first embodiment, even if the first overflow suction nozzle gets clogged, the second overflow suction nozzle performs the process of the first overflow suction nozzle instead. Therefore, there is no possibility that the liquid overflows immediately from the reaction vessel. Thus, the user can determine whether to continue the cleaning operation after the first overflow suction nozzle gets clogged according to the circumstances of the analysis operations of the automatic analyzer, which include the cleaning operation, at that time.

According to the first embodiment, it suffices that only one sensor serving as a clog detecting unit be provided. This reduces the number of components, and thus downsizes the device.

The sensor used in the first embodiment includes a pressure sensor, a capacitance sensor, a flow sensor, and a sensor for measuring a change in resistance between a plurality of electrodes.

Second Embodiment

Figure 12:
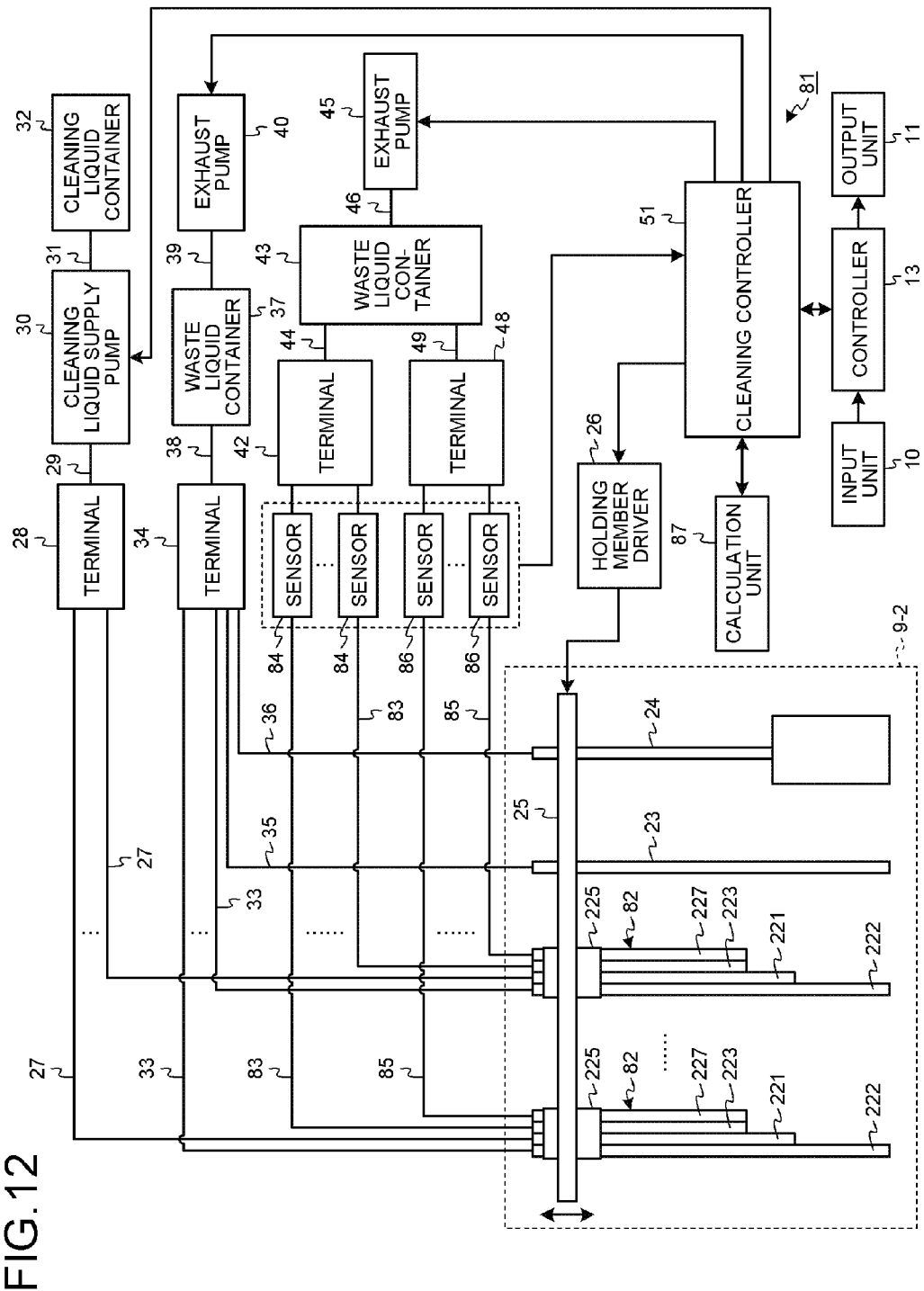
FIG. 12 is a diagram illustrating a configuration of a main part of a cleaning device according to a second embodiment of the present invention.

FIG. 12 is a diagram illustrating a main part of a cleaning device according to a second embodiment of the present invention. Parts of a cleaning device 81 illustrated in FIG. 12 having functional configurations similar to those of the cleaning device 21 explained in the first embodiment are denoted by the same reference numerals as those in FIG. 2.

The cleaning device 81 includes a plurality of nozzle groups 82. Each group has a set of four metal nozzles, each of which has different functions. The nozzle group 82 includes the cleaning liquid discharge nozzle 221, the liquid suction nozzle 222, the first overflow suction nozzle 223, and a second overflow suction nozzle 227 of which tip is positioned at the same level as the tip of the first overflow suction nozzle 223. The diameter of the second overflow suction nozzle 227 is equal to that of other nozzles. The second overflow suction nozzle 227 is arranged in parallel with other nozzles at least from a portion held by the cover 225 to the tip portion. The positional relationship between the four nozzles in the diametrical direction corresponds to that in FIG. 4 while the second overflow suction nozzle 224 is replaced with the second overflow suction nozzle 227.

The first overflow suction nozzle 223 is connected to the terminal 42 via a tube 83 (the first flow path). In the middle of the tube 83, is provided a sensor 84 (a first sensor) for detecting the flow of the liquid flowing through the tube 83 per time unit.

The second overflow suction nozzle 227 is connected to the terminal 48 via a tube 85 (a second flow path) having the same diameter as that of the tube 83. In the middle of the tube 85, is provided a sensor 86 (a second sensor) for detecting the volume of the liquid flowing through the tube 85 per time unit.

A reaction vessel cleaner 9-2 that includes the nozzle groups 82 contains the cleaning liquid suction nozzle 23; the drying nozzle 24; the nozzle groups 82; and the holding member 25 that holds the cleaning liquid suction nozzle 23 and the drying nozzle 24.

The cleaning device 81 is provided with a calculation unit 87 (calculation unit) that calculates a difference between the flows of the liquid, which are detected by the sensors 84 and 86. The calculation unit 87 calculates a difference between the flows of the liquid flowing through the first and the second overflow suction nozzles 223 and 227 both of which belong to the nozzle group 82, using the sensor signals from the sensors 84 and 86 that correspond respectively to the nozzles.

In the second embodiment, the level of the tip of the first overflow suction nozzle 223 and the level of the tip of the second overflow suction nozzle 227 are equal with each other. Thus, when the cleaning liquid discharge nozzle 221 discharges the cleaning liquid and thus the level of the liquid gradually rises, the first and the second overflow suction nozzles 223 and 227 start sucking the liquid approximately at the same time.

Figure 13:
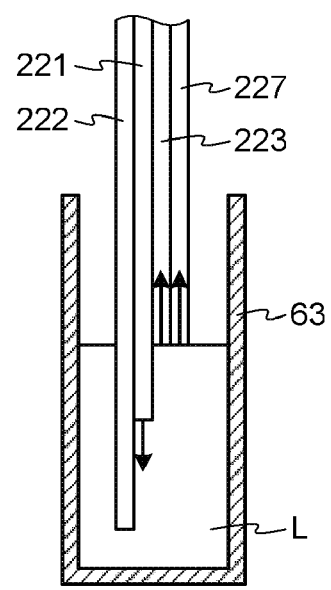
FIG. 13 is a diagram illustrating a state in the cleaning device according to the second embodiment of the present invention where a cleaning liquid discharge nozzle discharges cleaning liquid to a reaction vessel and first and second overflow suction nozzles suck liquid.

FIG. 13 is a diagram illustrating a state where the cleaning liquid discharge nozzle 221 discharges the cleaning liquid to the reaction vessel and the first overflow suction nozzle 223 and the second overflow suction nozzle 227 suck the liquid. As illustrated in FIG. 13, because the first and the second overflow suction nozzles 223 and 227 have equal diameters, they suck the liquid L at approximately the same rate due to driving of the exhaust pump 45. In addition, the tube 83 and the tube 85 have the same diameter. Thus, in the case where the first and the second overflow suction nozzles 223 and 227 normally operate without causing clog, the results of computation by the calculation unit 87, i.e., the difference between the outputs of the corresponding sensors 84 and 86, is approximately zero.

In the second embodiment, when the computation result is out of a predetermined range including zero, it is determined that clog is caused in one of the first overflow suction nozzle 223 and the second overflow suction nozzle 227. In this sense, the sensors 84 and 86 and the calculation unit 87 have functions of a clog detecting unit.

The method for controlling the cleaning operation performed by the automatic analyzer that includes the cleaning device 81 is similar to the method for controlling the cleaning operation explained in the first embodiment (see FIG. 6). At step S6, however, clog in the first overflow suction nozzle 223 or the second overflow suction nozzle 227 is detected on the basis of the result of computation by the calculation unit 87. At step S13, when even one of the differences between sensor outputs calculated with respect to the nozzle groups 82 by the calculation unit 87 is a value out of the predetermined range, error information is output from the output unit 11.

According to the second embodiment of the present invention, the two overflow suction nozzles are provided capable of sucking the liquid containing the cleaning liquid when the cleaning liquid is discharged to the liquid storage part of the vessel for storing the liquid. Thus, even if one of the overflow suction nozzles gets clogged, suction of the liquid can be continued with the other overflow suction nozzle. This definitely prevents the liquid, such as the cleaning liquid, from overflowing from the reaction vessel. Also, this extends the life of the overflow suction nozzles.

According to the second embodiment, an overflow suction nozzle without clog continues the suction operation. Therefore, even if clog in one of the overflow suction nozzles is detected, the following operations can be flexibly set depending on the operation state at that time.

The first and second embodiments are explained above as the best modes to carry out the present invention. However, the present invention should not be limited to these embodiments. For example, the number of overflow suction nozzles is not limited to two. It may be three or more.

In the present invention, the nozzle group may consist of three nozzles of a cleaning liquid discharge nozzle and first and second overflow suction nozzles, and a liquid suction nozzle may be separately provided. Such a configuration allows application of the present invention to a reaction vessel with smaller cross-sectional area.

In the present invention, a plurality of nozzles forming a set of nozzles group may be each positioned near other nozzles while being separated from each other.

As described above, the present invention may include various embodiments not described herein, and various design modifications may be made within the technical ideas specified by the claims.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cleaning device that cleans a liquid storage part of a vessel for storing liquid, the cleaning device comprising:
   a cleaning liquid discharge nozzle coupled to a cleaning liquid container storing cleaning liquid that discharges the cleaning liquid to the liquid storage part;
   a liquid suction nozzle of which tip is positioned below the cleaning liquid discharge nozzle configured to suck liquid stored in the liquid storage part;
   a first overflow suction nozzle of which tip is positioned above the tip of the cleaning liquid discharge nozzle, the first overflow suction nozzle coupled to an exhaust pump configured to suck liquid from the liquid storage part;
   a second overflow suction nozzle of which tip is positioned above the tip of the first overflow suction nozzle, the second overflow suction nozzle coupled to the exhaust pump configured to suck liquid from the liquid storage part; and
   a clog detecting unit coupled to the second overflow suction nozzle, wherein the clog detecting unit comprises at least one sensor operatively linked to a controller programmed to detect clog in the first overflow suction nozzle by detecting suction of liquid by the second overflow suction nozzle,
   wherein the cleaning liquid discharge nozzle, liquid suction nozzle, first overflow suction nozzle, and second overflow suction nozzle are held parallel in a nozzle group.

2. The cleaning device according to claim 1, wherein
the cleaning device comprises a plurality of nozzle groups, each comprising a cleaning liquid discharge nozzle, liquid suction nozzle, and first and second overflow suction nozzles, and
the at least one sensor can detect suction of liquid by any of the plurality of second overflow suction nozzles.

3. An automatic analyzer comprising a measuring unit configured to optically measure the result of a reaction of a specimen and reagent, and a data processing unit that is programmed to cause the specimen and a reagent to react with each other and control the measuring unit, wherein
the measuring unit comprises the cleaning device according to claim 1 as a unit for cleaning a liquid storage part of a reaction vessel in which the specimen and the reagent are caused to react with each other.

4. The automatic analyzer according to claim 3, further comprising:
an output unit coupled to the clog detecting unit that is programmed to output a result when the clog detecting unit detects clog in one of the first and second overflow suction nozzles, and request input of an instruction signal on whether to continue an operation being performed by the automatic analyzer.

5. The automatic analyzer of claim 4, further comprising
an input unit coupled to the clog detecting unit that is programmed to receive input of the instruction signal output by the output unit; and
an operation control unit programmed to perform operation control based on the instruction signal that is input by the input unit, wherein the operation control unit is coupled to the output unit, the input unit, and the exhaust pump and is part of the data processing unit.

6. The cleaning device according to claim 1, wherein the cleaning device is configured to insert the second overflow suction nozzle into the liquid storage part such that the tip of the second overflow suction nozzle is at the same height as or below an upper end surface of the vessel for storing liquid.

7. The cleaning device according to claim 1, wherein when the cleaning liquid discharge nozzle discharges the cleaning liquid, the controller is programmed to cause the first and second overflow suction nozzles to suck the liquid containing the cleaning liquid from the liquid storage part.

8. The cleaning device according to claim 1, wherein the at least one sensor comprises at least one of a photoelectric sensor, a photo interrupter, a pressure sensor, a capacitance sensor, a flow sensor, and a sensor for measuring a change in resistance between a plurality of electrodes.

9. The cleaning device according to claim 1, further comprising at least one additional overflow suction nozzle configured to suck the liquid containing the cleaning liquid from the liquid storage part.

10. The cleaning device according to claim 1, wherein the cleaning device is configured to insert the liquid suction nozzle into the liquid storage part such that the tip of the liquid suction nozzle is higher than a bottom surface of the vessel for storing liquid.

11. The cleaning device according to claim 1, wherein the diameters of the first and second overflow suction nozzles are equal to each other.

12. The cleaning device according to claim 1, wherein the at least one sensor comprises a first sensor that configured to detect flow of liquid flowing through a first flow path, wherein the first sensor is connected to the first overflow suction nozzle.

13. The cleaning device according to claim 12, wherein the at least one sensor further comprises a second sensor configured to detect flow of liquid flowing through a second flow path, wherein the second sensor is connected to the second overflow suction nozzle.

14. The cleaning device according to claim 13, wherein the clog detecting unit further comprises a calculation unit programmed to calculate a difference between the flows detected by the first and second sensors.

\* \* \* \* \*